(12) United States Patent
Wu et al.

(10) Patent No.: US 10,864,383 B2
(45) Date of Patent: Dec. 15, 2020

(54) RESPIRATORY GATING SYSTEM

(71) Applicants: SEOUL NATIONAL UNIVERSITY HOSPITAL, Seoul (KR); PAPRICA Lab. Co., Ltd., Seoul (KR)

(72) Inventors: Hong Gyun Wu, Seoul (KR); Jong Min Park, Seoul (KR); Chang Heon Choi, Bucheon-si (KR); Jung In Kim, Seoul (KR)

(73) Assignees: SEOUL NATIONAL UNIVERSITY HOSPITAL, Seoul (KR); PAPRICA Lab. Co., Ltd., Seoul (KR)

( * ) Notice: Subject to any disclaimer, the term of this patent is extended or adjusted under 35 U.S.C. 154(b) by 0 days.

(21) Appl. No.: 16/173,418

(22) Filed: Oct. 29, 2018

(65) Prior Publication Data

US 2019/0060668 A1    Feb. 28, 2019

Related U.S. Application Data

(63) Continuation of application No. PCT/KR2017/004585, filed on Apr. 28, 2017.

(30) Foreign Application Priority Data

Apr. 29, 2016   (KR) .................. 10-2016-0053175

(51) Int. Cl.
*A61N 5/10* (2006.01)
*A61N 5/00* (2006.01)

(52) U.S. Cl.
CPC .............. *A61N 5/107* (2013.01); *A61N 5/00* (2013.01); *A61N 5/10* (2013.01); *A61N 5/1067* (2013.01);

(Continued)

(58) Field of Classification Search
CPC ............... A61N 5/1037; A61N 5/1049; A61N 2005/1055; A61N 5/00; A61N 5/10;

(Continued)

(56) References Cited

U.S. PATENT DOCUMENTS 6,774,929 B1   8/2004 Kopp
6,862,469 B2 * 3/2005 Bucholz ............... A61N 5/1049
                                                324/307

(Continued)

FOREIGN PATENT DOCUMENTS

KR   20080039916 A   5/2008
KR   20140058313 A   5/2014

(Continued)

OTHER PUBLICATIONS

International Search Report dated Aug. 16, 2017.

(Continued)

*Primary Examiner* — Chih-Cheng Kao
(74) *Attorney, Agent, or Firm* — Dinsmore & Shohl LLP; Yongsok Choi, Esq.

(57) ABSTRACT

The present disclosure relates to a respiratory gating system for inducing respiration of a patient during radiation therapy. A respiratory gating system according to one embodiment of the present disclosure comprises: an image management unit for acquiring an MRI image of a patient and processing the acquired image; and a projection unit for displaying the MRI image acquired and processed by the image management unit to the patient in real time, wherein the projection unit may be configured to project an image of a treatment area of the patient in real time using, as a screen, a bore of a radiotherapy equipment which is formed to surround the patient in order to acquire the MRI image.

6 Claims, 5 Drawing Sheets

(52) U.S. Cl.
CPC .......... *A61N 5/1068* (2013.01); *A61N 5/1049* (2013.01); *A61N 2005/1055* (2013.01)

(58) Field of Classification Search
CPC .. A61N 5/1045; A61N 5/1067; A61N 5/1068; A61N 2005/1072; A61N 2005/1074; A61N 5/1039; A61N 5/107; A61N 5/1048; A61B 2576/02; A61B 5/0033; A61B 5/0046; A61B 5/0077; A61B 5/055; A61B 5/0816; A61B 5/1126; A61B 5/1127

See application file for complete search history.

(56) References Cited

U.S. PATENT DOCUMENTS

| | | | | |
|---|---|---|---|---|
| 2010/0008466 | A1* | 1/2010 | Balakin | H05H 13/04 378/62 |
| 2014/0121495 | A1* | 5/2014 | Dempsey | A61B 5/4848 600/411 |
| 2014/0125337 | A1* | 5/2014 | Lee | G01R 33/283 324/309 |
| 2015/0200996 | A1 | 7/2015 | Ziarati | |
| 2017/0281970 | A1* | 10/2017 | Han | A61B 5/1135 |
| 2019/0080459 | A1* | 3/2019 | Lachaine | A61N 5/107 |

FOREIGN PATENT DOCUMENTS

| | | |
|---|---|---|
| KR | 20150018238 A | 2/2015 |
| WO | 2016064204 A1 | 4/2016 |

OTHER PUBLICATIONS

Danny Lee, et al., "Audiovisual Biofeedback Improves Cine-Magnetic Resonance Imaging Measured Lung Tumor Motion Consistency," International Journal of Radiation Oncology, Biology, Physics, Nov. 18, 2015, vol. 94, Issue No. 3, pp. 628-636, Sidney & Newcastle, NSW, Australia.

Ellen M. Kerkof, et al., "A New Concept for Non-Invasive Renal Tumour Ablation Using Real-Time MRI-Guided Radiation Therapy," Journal Compilation, BJU International, Dec. 23, 2010, vol. 107, pp. 63-68, Department of Radiotherapy, Internal Medicine and Urology, University Medical Center Utrecht, Utrecht, The Netherlands.

Vijay R. Kini, et al., "Patient Training in Respiratory-Gated Radiotherapy," Journal, Medical Dosimetry, Jan. 1, 2003, vol. 28, Issue No. 1, pp. 7-11, Department of Radiation Oncology, Medical College of Virginia and the Hunter Holmes McGuire Veterans Medical Center, Richmond, Virginia.

* cited by examiner

10

RESPIRATORY GATING SYSTEM

CROSS-REFERENCE TO RELATED APPLICATIONS

This application is a continuation of PCT/KR2017/004585 filed on Apr. 28, 2017 which claims priority to Korean Patent Application No. 10-2016-0053175 filed on Apr. 29, 2016, the entire contents of which are herein incorporated by reference.

FIELD OF THE INVENTION

The present disclosure relates to a respiratory gating system, and more particularly, to a respiratory gating system capable of allowing a patient to control respiration to promote treatment by acquiring a real-time magnetic resonance imaging (MRI) image of a treatment region during radiation therapy and displaying the real-time MRI image to the patient.

BACKGROUND

In addition to surgery and chemotherapy, radiation therapy is one of the three major cancer treatment methods, and it is a treatment method of killing cancer cells by irradiating radiation to a tumor volume. Generally, radiation therapy is performed by establishing a treatment plan according to diagnosis using medical imaging devices such as a computerized tomography (CT) device, an MRI device, a positron emission tomography (PET), and the like and treating a tumor using ionizing radiation generated from a medical linear accelerator on the basis of the established treatment plan.

In the course of the radiation therapy, when radiation is delivered to a tumor volume, normal organs around the tumor volume may also be exposed to radiation. Thus, when establishing a radiation therapy plan, it is important to minimize radiation delivered to the normal organs around the tumor volume while the radiation is sufficiently delivered to kill cancer cells in the tumor volume.

As described above, various treatment methods for accurate radiation therapy, which include image-guided radiation therapy (IGRT), intensity modulated radiation therapy (IMRT), respiratory gated radiation therapy (RGRT), and the like, are known to minimize radiation transmission to surrounding normal organs while delivering sufficient radiation to the tumor volume.

Among these treatment methods, the RGRT is a therapy method of irradiating radiation in consideration of a movement of a tumor when a position of the tumor is changed due to respiration during radiation therapy for a thoracic region and an abdomen region. According to one known form of the RGRT, a marker placed outside a body of a patient is monitored in real time to acquire respiration cycle information, and the information is transmitted to a radiation therapy system, thereby performing treatment in a manner in which an irradiation time is interlocked with the movement of the tumor.

In such a conventional treatment method, the radiation therapy may be performed by interlocking the position of the tumor with the irradiation time according to the patient, and when the respiratory cycle is not constant, the irradiation time becomes longer and thus the treatment is not smoothly performed. Therefore, there is a method of training the patient to have a certain pattern of breathing, or a method of controlling breathing through breathing guidance through audio during treatment.

However, there is a limitation to maintaining a breathing pattern of patient constantly so that radiation therapy can be continued through the method of breathing guidance through audio, advance education, and training.

SUMMARY OF INVENTION

The present disclosure is directed to providing a respiratory gating system capable of reducing radiation therapy time by inducing a patient under respiration gating therapy to easily and accurately control breathing.

One aspect of the present disclosure provides a respiratory gating system for inducing respiration of a patient during radiation therapy, the respiratory gating system comprising an image management unit configured to acquire a magnetic resonance imaging (MRI) image of the patient and process the acquired MRI image, and a projection unit configured to display the MRI image acquired and processed in the image management unit to the patient in real time. The projection unit may be configured to project an image of a treatment region of the patient in real time using a bore of a radiation therapy apparatus, which is formed to surround the patient to acquire the MRI image, as a screen.

The projection unit may comprise a beam projector, and the beam projector may be disposed outside the bore of the radiation therapy apparatus.

The image management unit may comprise an image acquiring unit configured to acquire the MRI image of the patient, a first converter configured to convert the image acquired in the image acquiring unit into an editable format, an encoder configured to edit the image converted in the first converter, and a second converter configured to convert the image edited in the encoder into a format of an image to be projected on the screen. The first converter may receive a high definition multimedia interface (HDMI) video signal from the image management unit and convert the HDMI video signal into a video graphics array (VGA) video signal, and the second converter receives the VGA video signal from the encoder and converts the VGA video signal into an HDMI video signal. The encoder may enlarge a tumor part of the patient requiring treatment from the MRI image on the basis of the video signal transmitted from the first converter.

The respiratory gating system may further comprise a radiation irradiation unit configured to irradiate the patient with radiation according to the radiation therapy plan, and the radiation irradiation unit is configured to irradiate the radiation only when a predetermined condition is satisfied.

The radiation irradiation unit may be configured to irradiate the radiation only when the tumor requiring treatment is located within the predefined boundary on the basis of the MRI image acquired in the image management unit.

According to an aspect of the present disclosure, a MRI image is displayed in real time to allow a patient to see during radiation therapy such that the patient can directly observe a change in a position of a tumor due to respiration, Thus, the patient easily control respiration so that the tumor is in a position where predefined irradiation is possible, thereby significantly reducing the radiation therapy time.

DETAILED DESCRIPTION

Figure 1:
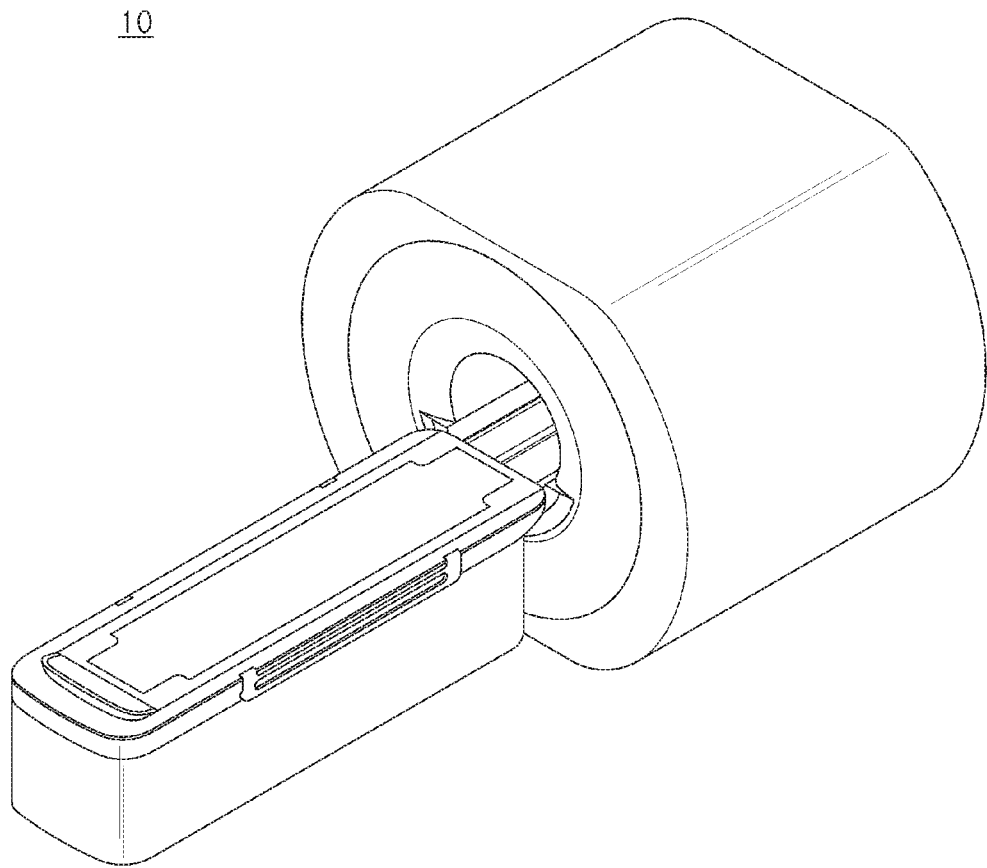
FIG. 1 is a diagram illustrating a schematic appearance of radiotherapy equipment for performing respiratory gated radiation therapy according to one embodiment of the present disclosure.

Hereinafter, embodiments of the present disclosure will be fully described in a detail which is suitable for implementation by those skilled in the art to which the present disclosure pertains with reference to the accompanying drawings.

In order to clearly describe the present disclosure, a portion not related to the present disclosure will be omitted, and throughout this disclosure, like reference numerals will be assigned to like components. Further, a size and the like of each component shown in the drawings are arbitrarily illustrated for convenience of description, and thus the present disclosure is not necessarily limited to those shown in the drawings.

That is, it should be noted that specific shapes, structures, and features described herein can be changed and implemented from one embodiment to another embodiment without departing from the spirit and scope of the present disclosure, and a position or an arrangement of each component can also be changed without departing from the spirit and scope of the present disclosure. Accordingly, the following detailed description is not to be taken in a limiting sense, and the scope of the present disclosure should be construed to include the scope of the appended claims and equivalents thereof.

FIG. 1 is a diagram illustrating a schematic appearance of radiotherapy equipment for performing respiratory gated radiation therapy according to one embodiment of the present disclosure. Referring to FIG. 1, radiotherapy equipment 10 is configured to move inside a bore in a state in which a patient is lying down to perform radiation therapy and capturing an image for radiation therapy.

A respiratory gating system according to one embodiment of the present disclosure can reduce a radiation therapy time by allowing the patient to easily control respiration in the case of performing respiratory gated radiation therapy in the radiotherapy equipment 10. The respiratory gating system according to the present embodiment will be described in detail below.

Figure 2:
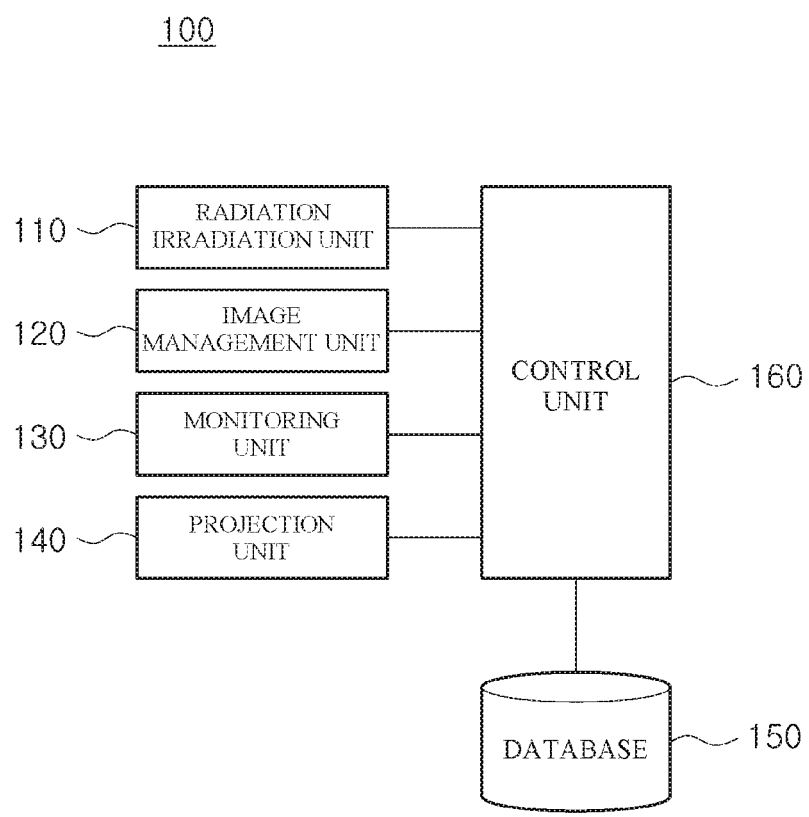
FIG. 2 is a diagram illustrating an internal configuration of a respiratory gating system according to one embodiment of the present disclosure.

FIG. 2 is a diagram illustrating a configuration of the respiratory gating system according to one embodiment of the present disclosure. Referring to FIG. 2, the respiratory gating system 100 may include a radiation irradiation unit 110, an image management unit 120, a monitoring unit 130, a projection unit 140, a database 150, and a control unit 160. The above-described components of the respiratory gating system 100 are illustrative and as necessary, at least in part of the components or functions of the respiratory gating system 100 may be included and implemented in the radiotherapy equipment 10, or may be implemented outside the radiotherapy equipment 10.

First, according to one embodiment of the present disclosure, the radiation irradiation unit 110 may perform a function of irradiating the patient with radiation according to a treatment plan. Specifically, the radiation irradiation unit 110 may include a linear accelerator having a shielding material such as a multileaf collimator to irradiate radiation with a predetermined pattern or signal. In this case, it is possible to control an amount and a range of the radiation being irradiated according to the treatment plan and to control the radiation only when a predetermined condition is satisfied.

For example, a boundary in a predetermined range around a tumor may be defined from an image of a tumor region of a patient acquired prior to radiation therapy, a position of the tumor may be tracked in real time during the radiation therapy, and radiation is controlled to be irradiated when the tumor is positioned within the defined boundary.

Figure 3A:
FIG. 3A is a diagram illustrating a position of a tumor and a boundary for irradiating radiation during respiratory gated radiation therapy.
Figure 3B:
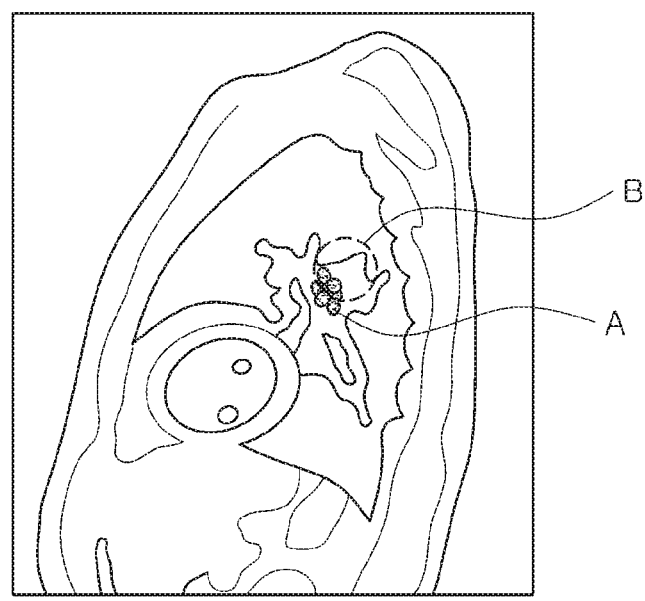
FIG. 3B is a diagram illustrating a position of a tumor and a boundary for irradiating radiation during respiratory gated radiation therapy.

FIGS. 3A and 3B are diagrams illustrating a position of a tumor and a boundary for irradiating radiation during respiratory gating radiation therapy. Referring to FIGS. 3A and 3B, the radiation irradiation unit 110 according to the present embodiment is configured such that when a position of a tumor A is changed due to respiration of the patient and the tumor A is positioned in a boundary B according to a treatment plan (FIG. 3A), radiation may be irradiated, and when the tumor A is out of the boundary B (FIG. 3B), irradiation of the radiation may be stopped. Accordingly, even though the position of the tumor is changed according to respiration of the patient, treatment according to the treatment plan may be performed.

Meanwhile, since a radiation therapy time is determined by a time at which the tumor A remains within the predefined boundary B, it is important for the patient to appropriately control respiration to allow the tumor A to remain within the predefined boundary B for a long period of time. A detailed configuration of the respiratory gating system for this purpose will be described below.

The image management unit 120 according to the present embodiment may perform a series of processes to acquire an image relating an anatomical structure of the patient before and during radiation therapy and to show the acquired image to a therapist or the patient. The acquisition of the image may be performed to establish the treatment plan before the radiation therapy, and it may also be performed to monitor a change in the position of the tumor in real time by respiration of the patient during the radiation therapy.

In the present embodiment, the image may be acquired through magnetic resonance imaging (MRI). The MRI may acquire an image of the inside of a human body using a magnetic field generated by a magnetic force, and it has advantage in that an excellent contrast and resolution image may be obtained while avoiding unnecessary radiation exposure as compared with a computerized tomography (CT).

As described below, the image management unit 120 may be interlocked with the projection unit 140 to allow the patient to directly confirm an image of a tumor region, and to this end, the image management unit 120 may process an acquired image through a series of processes.

Figure 4:
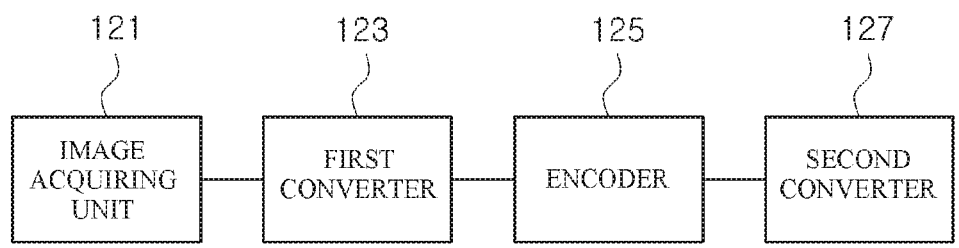
FIG. 4 is a diagram illustrating an internal configuration of an image management unit of a respiratory gating system according to one embodiment of the present disclosure.

FIG. 4 is a diagram illustrating an internal configuration of an image management unit of a respiratory gating system according to one embodiment of the present disclosure. Referring to FIG. 4, the image management unit 120 may include an image acquiring unit 121, a first converter 123, an encoder 125, and a second converter 127.

As described above, the image acquiring unit 121 may acquire the image of the tumor region of the patient through an MRI capturing or the like. The first converter 123 may receive a high definition multimedia interface (HDMI) video signal from the image acquiring unit 121 and convert the HDMI video signal into a video graphics array (VGA) video signal, and the VGA video signal converted in the first converter 123 may be transmitted to the encoder 125. The encoder 125 may edit an image on the basis of the transmitted VGA video signal. For example, since all the captured images are not required but only an image of the tumor region is required for respiration control of the patient, unnecessary parts of the image for the patient may be deleted and a required part may be enlarged. The image edited in the encoder 125 may be transmitted as a VGA video signal to the second converter 127, and the VGA video signal may be converted into an HDMI video signal in the second converter 127.

As such, the image management unit 120 may process an acquired image through a series of steps to display the image to the patient through the projection unit 140.

The monitoring unit 130 according to the present embodiment may perform a function of monitoring the image of the tumor region of the patient and a radiation irradiation status in real time in interlocking with the radiation irradiation unit 110 and the image management unit 120.

The monitoring unit 130 may monitor an operation status of the entire system by comprehensively checking the image acquired by the image management unit 120 and a status of the radiation irradiation unit 110. For example, the position of the tumor may be determined in real time from the image acquired by the image management unit 120, and a range in which the radiation is irradiated may be checked through an opening or closing state of the collimator of the linear accelerator and whether or not the radiation is irradiated. Thus, it is possible to monitor whether the respiratory gating system 100 is operating normally. Further, the monitoring unit 130 may directly display the image acquired from the image management unit 120 or may display an edited image through an image processing.

The projection unit 140 according to the present embodiment may perform a function of displaying the image acquired through the image management unit 120 to the patient. To this end, the projection unit 140 may include a beam projector.

According to one embodiment of the present disclosure, the image management unit 120 may be interlocked with the projection unit 140 in addition to the monitoring unit 130, and the projection unit 140 may project the image acquired and processed in the image management unit 120 on a position at which the patient may see during radiation therapy, e.g., on a bore surrounding the patient during treatment.

Figure 5:
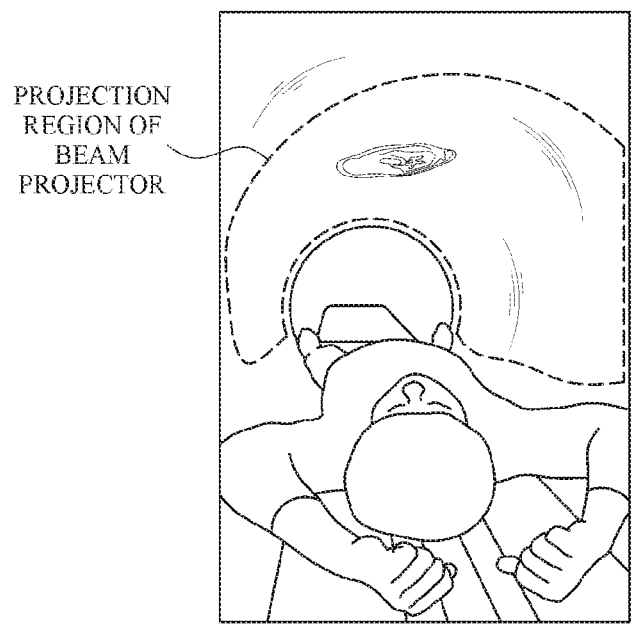
FIG. 5 is a diagram illustrating a case in which an image of a treatment region is displayed to a patient during radiation therapy according to one embodiment of the present disclosure.

FIG. 5 is a diagram illustrating a case in which an image of a treatment region is displayed to a patient during radiation therapy through a beam projector in the respiratory gating system according to one embodiment of the present disclosure. Referring to FIG. 5, the projection unit 140 according to the present embodiment projects an image in real time on an upper portion of the bore of the radiotherapy equipment 10 to allow the patient during radiation therapy to check a change in the position of the tumor in response to respiration. Accordingly, the patient may determine the change in the position of the tumor by his or her respiration in real time, and the patient may control his or her respiration to locate the tumor within a boundary at which radiation is irradiated.

As such, the projection unit 140 may project the image through the beam projector to the upper portion of the bore of the radiotherapy equipment 10 as a screen. However, since a magnetic field is formed during an MRI capturing, there is restriction in that an electronic device cannot be placed in the bore. Therefore, in the present embodiment, electric and electronic equipment such as the beam projector constituting the projection unit 140 are disposed outside the bore so as not to be influenced by the magnetic field, and are arranged to project the image on the upper portion of the bore. For example, the beam projector and a connection cable constituting the projection unit 140 may be disposed on an inlet side of the bore or a side opposite of the inlet side thereof.

According to the arrangement of such a beam projector or the like, the image may be obliquely projected and distortion may occur in the projected image. Such distortion may be corrected through a keystone correction technique. The keystone correction technique may employ a known technique, and it is not included in the scope of the present disclosure so that a detailed description thereof will be omitted.

The database 150 according to the present embodiment may store basic information for radiation irradiation, an image management, an image projection, and the like. For example, information on a physical condition of an individual patient, a treatment plan established before radiation therapy, a location of a tumor, and an irradiation area and dose of radiation may be stored. Although the database 150 has been illustrated as being included in the respiratory gating system 100 in FIG. 2, the database 150 may be separately configured from the respiratory gating system 100 according to the needs of a skilled person implementing the present disclosure. Meanwhile, the database 150 in the present disclosure is a concept including a computer-readable recording medium and may be not only a database in a narrow sense but also a database in a broad sense including a data record based on a file system, and even a simple set of logs, if it is possible to retrieve and extract data.

Lastly, the control unit 160 according to the present embodiment may perform a function of controlling signals and a data flow between the radiation irradiation unit 110, the image management unit 120, the monitoring unit 130, the projection unit 140, and the database 150. That is, the control unit 160 controls the signals and the data flow from the outside or between the components of the respiratory gating system 100, thereby allowing the radiation irradiation unit 110, the image management unit 120, the monitoring unit 130, the projection unit 140, and the database 150 to perform their inherent functions.

While the present disclosure has been described with reference to specific items such as particular components, exemplary embodiments, and drawings, these are merely provided to help understanding the present disclosure, and the present disclosure is not limited to these embodiments, and those skilled in the art to which the present disclosure pertains can variously alter and modify from the description of the present disclosure.

Therefore, the spirit of the present disclosure should not be limited to the above-described embodiments, and it should be construed that the appended claims as well as all equivalents or equivalent modifications of the appended claims will fall within the scope of the present disclosure.

What is claimed is:

1. A respiratory gating system for inducing respiration of a patient during radiation therapy, the respiratory gating system comprising:

an image management unit configured to acquire a magnetic resonance imaging (MRI) image of the patient and process the acquired MRI image;
a projection unit configured to display the MRI image acquired and processed in the image management unit to the patient in real time; and
a radiation irradiation unit configured to irradiate the patient with radiation according to a radiation therapy plan,
wherein the projection unit is configured to project an image of a treatment region of the patient in real time together with a predefined boundary according to the radiation therapy plan using a bore of a radiation therapy apparatus, which is formed to surround the patient to acquire the MRI image, as a screen.

2. The respiratory gating system of claim 1, wherein the projection unit comprises a beam projector, and the beam projector is disposed outside the bore of the radiation therapy apparatus.

3. The respiratory gating system of claim 1, wherein the image management unit comprises:
an image acquiring unit configured to acquire the MRI image of the patient;
a first converter configured to convert the image acquired in the image acquiring unit into an editable format;
an encoder configured to edit the image converted in the first converter; and
a second converter configured to convert the image edited in the encoder into a format of an image to be projected on the screen.

4. The respiratory gating system of claim 3, wherein:
the first converter receives a high definition multimedia interface (HDMI) video signal from the image management unit and converts the HDMI video signal into a video graphics array (VGA) video signal; and
the second converter receives the VGA video signal from the encoder and converts the VGA video signal into an HDMI video signal.

5. The respiratory gating system of claim 3, wherein the encoder enlarges a tumor part of the patient requiring treatment from the MRI image on the basis of a video signal transmitted from the first converter.

6. The respiratory gating system of claim 1, wherein the radiation irradiation unit is configured to irradiate radiation only when a tumor that requires treatment is located within the predefined boundary on the basis of the MRI image acquired in the image management unit.

* * * * *